United States Patent
Shanbhag et al.

(10) Patent No.: US 9,146,289 B2
(45) Date of Patent: Sep. 29, 2015

(54) TARGETED THERMAL TREATMENT OF HUMAN TISSUE THROUGH RESPIRATORY CYCLES USING ARMA MODELING

(75) Inventors: Dattesh Dayanand Shanbhag, Bangalore (IN); Thomas Kwok-Fah Foo, Clifton Park, NY (US); James Chapman Ross, Cambridge, MA (US); Rekha Venkatesan Tranquebar, Bangalore (IN); Siddharth Vikal, Punjab (IN)

(73) Assignee: General Electric Company, Niskayuna, NY (US)

( * ) Notice: Subject to any disclaimer, the term of this patent is extended or adjusted under 35 U.S.C. 154(b) by 1475 days.

(21) Appl. No.: 12/645,891

(22) Filed: Dec. 23, 2009

(65) Prior Publication Data

US 2011/0152666 A1    Jun. 23, 2011

(51) Int. Cl.
  *A61B 5/05* (2006.01)
  *G01R 33/48* (2006.01)
  *A61N 7/02* (2006.01)
  A61B 5/055 (2006.01)
  A61B 5/08 (2006.01)
  A61B 5/113 (2006.01)
  A61B 17/00 (2006.01)
  A61B 19/00 (2006.01)

(52) U.S. Cl.
  CPC ............... *G01R 33/4804* (2013.01); *A61N 7/02* (2013.01); *A61B 5/055* (2013.01); *A61B 5/08* (2013.01); *A61B 5/113* (2013.01); *A61B 2017/00084* (2013.01); *A61B 2017/00699* (2013.01); *A61B 2019/5236* (2013.01); *G01R 33/4814* (2013.01)

(58) Field of Classification Search
  None
  See application file for complete search history.

(56) References Cited

U.S. PATENT DOCUMENTS

| | | | |
|---|---|---|---|
| 6,587,707 B2 | 7/2003 | Nehrke et al. | |
| 6,621,889 B1 | 9/2003 | Mostafavi | |
| 6,687,625 B2 | 2/2004 | Srinivasan et al. | |
| 6,757,423 B1 | 6/2004 | Amini | |
| 6,863,655 B2 | 3/2005 | Bjaerum et al. | |
| 7,365,543 B2 | 4/2008 | Yui et al. | |
| 2002/0180436 A1* | 12/2002 | Dale et al. | 324/307 |
| 2003/0220557 A1 | 11/2003 | Cleary et al. | |
| 2005/0080333 A1 | 4/2005 | Piron et al. | |
| 2006/0002630 A1 | 1/2006 | Fu et al. | |
| 2006/0004547 A1 | 1/2006 | Mostafavi | |
| 2006/0293598 A1 | 12/2006 | Fraser | |
| 2007/0055140 A1 | 3/2007 | Kuroda | |
| 2007/0167784 A1 | 7/2007 | Shekhar et al. | |
| 2007/0205769 A1 | 9/2007 | Yui et al. | |
| 2007/0232882 A1 | 10/2007 | Glossop et al. | |
| 2007/0280556 A1 | 12/2007 | Mullick et al. | |
| 2008/0031404 A1 | 2/2008 | Khamene et al. | |
| 2008/0039746 A1 | 2/2008 | Hissong et al. | |
| 2008/0081991 A1* | 4/2008 | West et al. | 600/425 |
| 2008/0123927 A1 | 5/2008 | Miga et al. | |
| 2008/0144908 A1 | 6/2008 | West et al. | |
| 2008/0212737 A1 | 9/2008 | D'Souza et al. | |
| 2008/0231271 A1 | 9/2008 | Yui et al. | |
| 2009/0010540 A1 | 1/2009 | Mullick et al. | |
| 2009/0112132 A1* | 4/2009 | Chang et al. | 601/3 |
| 2009/0131782 A1* | 5/2009 | Moonen et al. | 600/411 |
| 2009/0161931 A1 | 6/2009 | Tao et al. | |
| 2009/0221902 A1* | 9/2009 | Myhr | 600/411 |

FOREIGN PATENT DOCUMENTS

WO    9501125 A1    1/1995

OTHER PUBLICATIONS de Senneville, B. D., et al, "Real-Time Adaptive Methods for Treatment of Mobile Organs by MRI-Controlled High-Intensity Focused Ultrasound", Magnetic Resonance in Medicine 57:319-330 (2007).
McClelland, J. R., et al., "A continuous 4D motion model from multiple respiratory cycles for use in lung radiotherapy", Medical Physics, vol. 33, No. 9, 3348-3358, Sep. 2006.
Pernot, M., et al., "Feasibility of Real-Time Motion Correction for HIFU Applications", IEEE Ultrasonics Symposium, 998-1001, 2003.
Rohlfing, T., et al., "Modeling liver motion and deformation during the respiratory cycle using intensity-based free-form registration of gated MR images", Visualization, Display, and Image-Guided Procedures, Seong Ki Mun, Editor, Proceedings of SPIE vol. 4319 (2001), pp. 337-348.
von Siebenthal, M., et al., "4D MR imaging of respiratory organ motion and its variability", Phys. Med. Biol. 52 (2007) 1547-1564.

\* cited by examiner

*Primary Examiner* — Unsu Jung
*Assistant Examiner* — Shahdeep Mohammed
(74) *Attorney, Agent, or Firm* — Melissa K. Dobson

(57) ABSTRACT

The present application discloses a technique for targeting therapeutic thermal energy to human tissue that is subject to displacement during a respiratory cycle using ARMA modeling. It discloses using an ARMA treatment of MRI tracking data of salient features of the tissue of interest to predict the spacial position of the portion of the tissue to be treated and using this prediction to guide the application of the thermal energy. It also discloses that this technique is particularly useful when the tissue of interest undergoes elastic deformation in a respiratory cycle and high energy focused ultrasound (HIFU) is used to ablate diseased tissue such as a cancerous tumor.

15 Claims, No Drawings

TARGETED THERMAL TREATMENT OF HUMAN TISSUE THROUGH RESPIRATORY CYCLES USING ARMA MODELING

BACKGROUND

The invention relates generally to a method of tracking the motion of the elements of a human tissue which is deformed during a respiratory cycle using ARMA modeling and using this tracking to target therapeutic thermal energy on a diseased portion of the tissue through multiple respiratory cycles. The thermal treatment, particularly the thermal ablation, of lesions, tumors or other diseased tissue has been practiced for some time. More recently high intensity focused ultrasound (HIFU) has been used to reach internal tissue using magnetic resonance imaging (MRI) to locate the appropriate focal point for the HIFU. In such applications MRI has been used to create thermal maps so that the effect of the application of the HIFU can be tracked and adjusted in real time with the aim that the diseased tissue is ablated while the healthy surrounding tissue is not adversely affected. A difficulty has arisen in applying this technique to tissue that is subject to displacement and elastic deformation during a respiratory cycle. One approach has been to gate the application of thermal energy such as HIFU so that it is only applied at a particular point in the respiratory cycle and assume that a given element of a tissue of a quiescent subject will return to the same location at a given point in the respiratory cycle. Another approach has been to track the portion of a tissue that is the object of thermal treatment in real time as the thermal energy is being applied. However, this requires frequent cycling of the MR apparatus between mapping the location of the portion of the tissue under treatment and thermal mapping to monitor the result of applying the thermal energy. Both of these approaches cause a significant lengthening of the time of treatment because for significant periods during the overall treatment thermal energy may not be appropriately applied. One needs to await a given window in the respiratory cycle or the availability of the MR apparatus for thermal mapping.

Yet another approach has been to develop a mathematical model, which predicts the locations of the elements of a given tissue subject to displacement during respiration so that the location of an element that is the target of thermal treatment can be predicted throughout a respiratory cycle. The model is developed by observation of the tissue of interest through multiple respiratory cycles. However, these models have been developed using a harmonic motion approach. Such models do not have adequate predictive power for tissues that undergo elastic deformation through a respiratory cycle and do not deal with changes in the elastic properties of the element of a tissue undergoing treatment. For instance a lesion being subjected to thermal ablation typically becomes stiffer and thus exhibits changes in its elastic behavior as treatment progresses.

BRIEF DESCRIPTION

The present invention involves a process for the targeted thermal treatment of internal human tissue which is subject to displacement during a respiratory cycle that includes deformable registration and creating an Autoregressive Moving Average (ARMA) based model of the tissue targeted for thermal therapy and using the model to guide the application of thermal energy over multiple respiratory cycles. In one embodiment the targeted tissue is subject to elastic deformation over the course of a respiratory cycle.

The model is conveniently created by tracking the spatial position of salient features representative of different portions of the tissue of interest with MRI over multiple respiratory cycles for a number of subjects and subjecting the data so collected to deformable/elastic registration and ARMA treatment. In one embodiment the displacement which is considered is limited to two dimensions. For instance in the case of liver tissue displacement out of the coronal plane is not modeled or tracked. The data is conveniently used as a training set to, with the help of ARMA analysis, create predictive relationships between a respiratory cycle and the location of the portions of the tissue of interest. It is helpful in the creation of the model to cluster field vectors using similarity criteria and to generate iso-motion contours.

The model may then be fitted to a given subject by tracking the spatial position of salient features representative of different portions of the tissue of interest with MRI over multiple respiratory cycles for that subject. In this way an individualized model can be created for each subject.

The individualized model can then be used to guide the application of thermal energy to a particular portion of the tissue of interest without the need to continuously track the movement of said portion during the application of the thermal energy. In one embodiment a lesion targeted for thermal ablation can be subjected to HIFU for five to ten minutes without resort to MRI tracking of the lesion. Thus the MR apparatus is fully available for thermal mapping so that the delivery of the thermal energy can be monitored without interruption for tracking of the lesion through the respiratory cycle.

The individualized model can be validated by occasionally actually tracking the tissue of interest by MRI during the thermal treatment. A typical thermal treatment might last about two hours and a validation tracking could be conducted about every five to ten minutes.

The validation data can then be used to assess the accuracy of the individualized model and determine if any errors are correctable or if use of the model should be terminated. In one embodiment the model can be updated during the course of thermal treatment to reflect changes in the elastic properties of the portion of the tissue undergoing thermal treatment. For instance, it is typical for tissue to become stiffer as it is subjected to thermal ablation and the individualized model could be adjusted to reflect this change in elastic properties. An error threshold can be set to determine if the individualized model predictions are sufficiently different from the actual tracking results to justify terminating the use of the model. In such a case the treatment could then continue by simply interspersing tracking and thermal mapping on an approximately one for one basis.

DETAILED DESCRIPTION

The present invention is concerned with the creation, validation and adjustment of a model to predict the spatial position of tissue of interest in a human subject over a respiratory cycle and using the model to guide the application of therapeutic thermal energy to a selected portion of the tissue of interest. The model is conveniently created by the use of deformable/elastic tracking of salient features of the tissue of interest, imaged using MRI, over a number of respiratory cycles and then a treatment of the resultant data by ARMA to yield an algorithm that relates spatial position to a time point in the respiratory cycle. The model can then be used to direct the targeting of thermal energy. The application of the thermal energy is typically done in conjunction with MRI thermal mapping so that the ability to target the thermal energy without tracking the tissue motion through every respiratory cycle allows thermal mapping and therefore thermal energy application without interruption for tissue tracking. This in turn allows a meaningful reduction in the treatment time. The model can be validated and modified by performing a tissue tracking during the course of thermal treatment and comparing the actual position of salient features through the respiratory cycle to those predicted by the model. One convenient modification is adjusting the model to account for the change in elasticity of the portion of the tissue of interest that is undergoing thermal treatment. Typically thermal treatment, particularly thermal ablation, will result in a loss of elasticity. This tracking can also be used to determine whether the model is redeemable or is no longer useful. One approach is to set a threshold error measurement to determine whether the model will be corrected or abandoned.

The creation of the model involves selecting a tissue that undergoes displacement during a respiratory cycle. The model can be of particular usefulness if the tissue undergoes elastic deformation during a respiratory cycle. This would include kidney and liver tissue.

It is convenient to only consider displacement within a given plane both for the creation of a model and for gathering the tracking data. For instance in the case of liver tissue the displacement as a result of respiration out of the coronal plane is known to be rather minimal. Thus it can be disregarded. On the other hand, because the displacement is so minimal the signal to noise ratio poses problems with tracking such displacement. However, with the appropriate data gathering and processing the model can be applied to 3D space. Techniques for the handling of image registration in 3D space are disclosed in U.S. Published Patent Applications 2009/0161931 and 209/0010540, incorporated by reference herein. Techniques for 3D image registration involving target deformation are disclosed in U.S. Published Application 2007/0280556 incorporated herein by reference.

The next step is to select salient features on the tissue of interest whose spatial location can be tracked through a respiratory cycle using MRI. It is convenient to use fiducials such as blood vessels as the salient features to be tracked. However, any feature that can be distinguished by MRI can be utilized. The features should be selected to be representative of the various portions or elements of the tissue of interest. The aim is to be able to predict the spatial location of a volume to be subjected to thermal treatment such as thermal ablation through a respiratory cycle. There can be advantages to selecting salient features which all lie outside the volume of tissue which is to be subjected to thermal treatment.

Then the movement of the salient features is tracked by MRI through a number of respiratory cycles. A sufficient number of cycles should be utilized to average out any idiosyncrasies of a particular respiratory cycle and yield data representative of a typical or average respiratory cycle. The tracking should be performed on quiescent subjects so that the displacements observed are all properly attributable to respiratory displacement.

The data obtained from the tracking is then subjected to ARMA analysis to yield an algorithm that will relate spacial position to a time point in the respiratory cycle. The aim is to be able to assign a precise position to the volume to be subjected to thermal treatment at each time point in a respiratory cycle. The ARMA treatment is viewed as more robust and as more likely to yield a reliable model than other modeling techniques such as those based upon harmonic motion.

The tracking data can be viewed as a training set that can inform the ARMA analysis in creating a useful algorithm. For each salient feature that is tracked a correlation between its spatial location and the time point in the respiratory cycle can be generated. The correlation can than be expanded to the volume of interest of which the salient features are representative.

The algorithm can then be applied to guide the application of therapeutic thermal energy. In one embodiment the thermal energy is used to ablate diseased tissue such as neoplastic tissue. Thus the algorithm can be usefully employed to guide the thermal ablation of cancerous tumors though it can also be usefully employed to ablate other undesirable lesions. In this regard, such diseased tissue may deform as a result of a respiratory cycle differently than the healthy tissue that surrounds it.

The use of the algorithm to target the thermal energy has the advantage that it can automatically account for the delay in communicating the target position to the thermal energy application means and the delay in retargeting the application means. For a given system these delays can be determined and then the interface between the algorithm or model and the application means adjusted so the thermal energy arrives at the position predicted for a time point in the respiratory cycle after these delays.

The therapeutic thermal energy can be delivered by any means that can be conveniently targeted to diseased tissue and can deliver the needed thermal energy over a reasonable time period. In this regard, it is desirable that the delivery means be capable of being rapidly retargeted so that it can follow the spacial displacement of the target tissue through a respiratory cycle. High intensity focused ultrasound (HIFU) is a particularly convenient delivery mechanism from the point of view of targeting and delivery per unit time.

The application of the thermal energy is typically monitored by MRI temperature mapping. It is convenient to deliver some thermal energy, check the results of the delivery with MRI temperature mapping and then deliver some further thermal energy. The aim is to raise the temperature of the targeted, typically diseased, tissue above the temperature needed for necrosis while minimizing the temperature increase of the surrounding tissue so as to avoid unduly harming healthy tissue.

The application of thermal energy and the MRI temperature mapping monitoring is typically interrupted a few times during the thermal treatment to validate and adjust the spatial algorithm. A typical treatment consumes a few hours and it is convenient to interrupt treatment for validation about every three minutes or more with validation interruption every five to ten minutes being particularly helpful.

The validation and adjustment involves tracking the salient features upon which the spatial algorithm was based and comparing their actual locations through the respiratory cycle to those predicted by the algorithm. The tracking is typically conducted over several respiratory cycles and a representative position is determined for each salient feature at each respiratory cycle time point evaluated.

The validation may usefully include an evaluation of whether some measure of the errors in the predicted spatial positions provided by the algorithm has exceeded some threshold. The threshold may be conveniently set at some value that is expected to define the point at which the algorithm is far enough out of synch with reality to justify abandoning its use. If the use of the model or algorithm is abandoned typically treatment would continue with a stricter alternation between thermal mapping and position tracking.

The adjustment may address drift in the predicted spatial values over numerous respiratory cycles and it may address changes in the elastic properties of the tissue undergoing thermal treatment. It may be that over the multiple respiratory cycles (at the normal adult respiration rate of 12 breaths per minute and a validation run every five minutes there are 60 cycles between validation runs) minor errors in spatial position predictions have compounded to the point where a correction is appropriate. In those instances in which the tissue of interest suffers elastic deformation during a respiratory cycle the elastic properties of the tissue volume being subjected to thermal treatment or ablation is likely to have changed its elastic properties as a result of the treatment. It is not uncommon for such volumes to become stiffer with treatment. This change can be detected from the validation runs and appropriate adjustments can be made in the model parameters.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A process for an in-vivo targeted thermal treatment of biological tissue of a subject which undergoes elastic deformation during a respiratory cycle comprising:
    creating a model which predicts the motion of said tissue during a respiratory cycle by an elastic registration and an autoregressive moving average (ARMA) treatment of a training set of data, wherein the training set of data is created by tracking spatial positions of one or more salient features representative of different portions of said tissue with magnetic resonance imaging (MRI) over multiple respiratory cycles of one or more subjects;
    using said model to target heat energy to a desired portion of said tissue over multiple respiratory cycles using said model;
    generating MRI thermal maps of said tissue and monitoring the thermal treatment with the MRI thermal maps;
    tracking actual positions of said salient features over one or more respiratory cycles of the subject;
    determining a change in elastic properties of said tissue of the subject at one or more determined intervals of time based on a difference between the tracked positions and positions of said salient features predicted by said model;
    updating the model to reflect the change in elastic properties of said tissue if the difference between the tracked positions and predicted positions is less than a given threshold and continue using the updated model to target heat energy to the desired portion of said tissue; and
    discontinuing use of the model and interspersing tracking and thermal mapping of the salient features of said tissue over subsequent respiration cycles if the difference between the tracked positions and predicted positions exceeds said threshold.

2. The process of claim 1 wherein said model includes a registration of the positions of said salient features over a projected respiratory cycle.

3. The process of claim 1 wherein said model includes a factor to account for the change in the elastic properties of the portion of said tissue subjected to said thermal treatment as a result of said treatment.

4. The process of claim 1 wherein said tissue is the liver.

5. The process of claim 1 wherein said thermal energy is provided by high intensity focused ultrasound (HIFU).

6. The process of claim 1 wherein the MRI thermal maps of said tissue are generated without interruption during at least about 3 minutes of said thermal treatment.

7. The process of claim 1 wherein the MRI thermal maps of said tissue are generated without interruption over multiple respiratory cycles during said thermal treatment.

8. The process of claim 7 wherein said model is validated by interrupting said MRI thermal mapping after multiple respiratory cycles, tracking the actual positions of said salient features of said tissue being subjected to thermal treatment over one or more respiratory cycles and comparing said positions to those predicted by said model.

9. The process of claim 8 wherein said validation is only performed after a plurality of respiratory cycles to yield data representative of an average respiratory cycle.

10. The process of claim 9 wherein said validation is performed between about every 5 and 10 minutes of said thermal treatment.

11. The process of claim 1 wherein said salient features are blood vessels.

12. The process of claim 1 wherein said salient features are selected so that none are within the portion of said tissue to be subjected to said thermal treatment.

13. The process of claim 1 wherein the portion of said tissue being subjected to thermal treatment is abnormal and deforms during a respiratory cycle differently than normal tissue.

14. The process of claim 13 wherein the abnormal tissue is diseased tissue.

15. The process of claim 14 wherein the abnormal tissue is a cancerous tumor.

* * * * *